United States Patent [19]

Talonn et al.

[11] Patent Number: 5,395,339
[45] Date of Patent: Mar. 7, 1995

[54] MEDICAL DEVICE WITH STERILE FLUID PATHWAY

[75] Inventors: Daniel A. Talonn, University City, Mo.; Roger L. Crouse, Ormond Beach, Fla.; Edwin G. Weichselbaum, Eureka, Mo.

[73] Assignee: Sherwood Medical Company, St. Louis, Mo.

[21] Appl. No.: 829,805

[22] Filed: Jan. 31, 1992

[51] Int. Cl.⁶ .................................................. A61M 5/00
[52] U.S. Cl. .................................... 604/111; 604/110
[58] Field of Search ............... 604/110, 111, 187, 218, 604/220, 221, 222, 199; 128/919

[56] References Cited

U.S. PATENT DOCUMENTS

| Re. 25,113 | 1/1962 | Wilburn ............... 604/190 |
|---|---|---|
| 2,972,991 | 2/1961 | Burke . |
| 3,008,570 | 11/1961 | Roehr et al. ............. 206/43 |
| 3,306,291 | 2/1967 | Burke . |
| 3,366,113 | 1/1968 | Hobbs . |
| 3,381,813 | 5/1968 | Coanda et al. ............ 206/63.2 |
| 3,416,657 | 12/1968 | Sorensen, Jr. et al. ............ 206/47 |
| 3,478,937 | 11/1969 | Solowey ................. 222/386 |
| 3,485,239 | 12/1969 | Vanderbeck . |
| 3,828,775 | 8/1974 | Armel . |
| 4,027,669 | 6/1977 | Johnston et al. . |
| 4,030,498 | 6/1977 | Tompkins . |
| 4,106,622 | 8/1978 | Windischman ............ 206/365 |
| 4,148,316 | 4/1979 | Xanthopoulos . |
| 4,178,930 | 12/1979 | Fisher, Jr. . |
| 4,181,223 | 1/1980 | Millet ................. 206/365 |
| 4,300,678 | 11/1978 | Gyure et al. ............ 206/364 |
| 4,367,738 | 1/1983 | Legendre et al. ............ 604/218 X |
| 4,781,684 | 11/1988 | Trenner ................. 604/110 |
| 4,832,695 | 5/1989 | Rosenberg et al. ............ 604/111 |
| 4,872,552 | 10/1989 | Unger ................. 206/365 |
| 4,897,083 | 1/1990 | Martell ............... 604/192 |
| 4,929,232 | 5/1990 | Sweeney et al. ............ 604/111 |
| 4,932,941 | 6/1990 | Min et al. ............... 604/110 |
| 4,979,943 | 12/1990 | Trenner ................. 604/110 |
| 4,994,034 | 2/1991 | Botich et al. ............ 604/110 |
| 5,024,661 | 6/1991 | Wender et al. ............ 604/110 |
| 5,026,354 | 6/1991 | Kocses ................. 604/195 |
| 5,037,393 | 8/1991 | Ellgass ................. 604/110 |
| 5,053,018 | 10/1991 | Talonn et al. ............ 604/198 |
| 5,090,962 | 2/1992 | Landry et al. ............ 604/110 |
| 5,106,372 | 4/1992 | Ranford ................. 604/110 |
| 5,163,918 | 11/1992 | Righi et al. ............ 604/198 |
| 5,232,459 | 8/1993 | Hjertman ................. 604/208 |

FOREIGN PATENT DOCUMENTS

| 0307367 | 3/1989 | European Pat. Off. ............ 604/110 |
|---|---|---|
| 2503032 | 9/1982 | Germany ................. A61M 5/18 |
| 9004424 | 5/1990 | WIPO ................. A61M 5/315 |

OTHER PUBLICATIONS

CA Abstract of DE 2503032.

Primary Examiner—C. Fred Rosenbaum
Assistant Examiner—V. Alexander
Attorney, Agent, or Firm—Montgomery W. Smith; Richard D. Allison; David A. Warmbold

[57] ABSTRACT

A self packaged medical device, such as a syringe assembly, having a hollow body and an operative element therein for the controlled dispensing or entry of fluid into the body. An extension member operatively connected to the operative element and extending proximally beyond the proximal end of the body. The device further including a proximal barrier between the extension member and the body and a distal barrier to maintain the sterility of the interior of the device prior to use. The medical device is also disclosed in combination with a safety syringe wherein a needle protective shield is movably mounted about the body and is movable between retracted and extended positions.

11 Claims, 6 Drawing Sheets

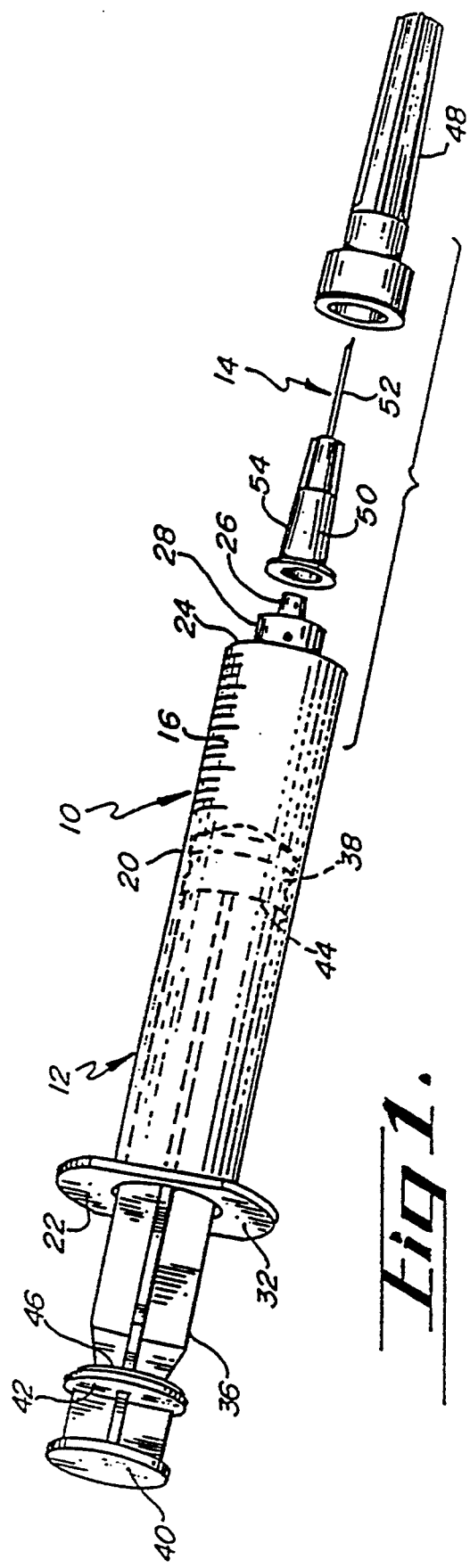
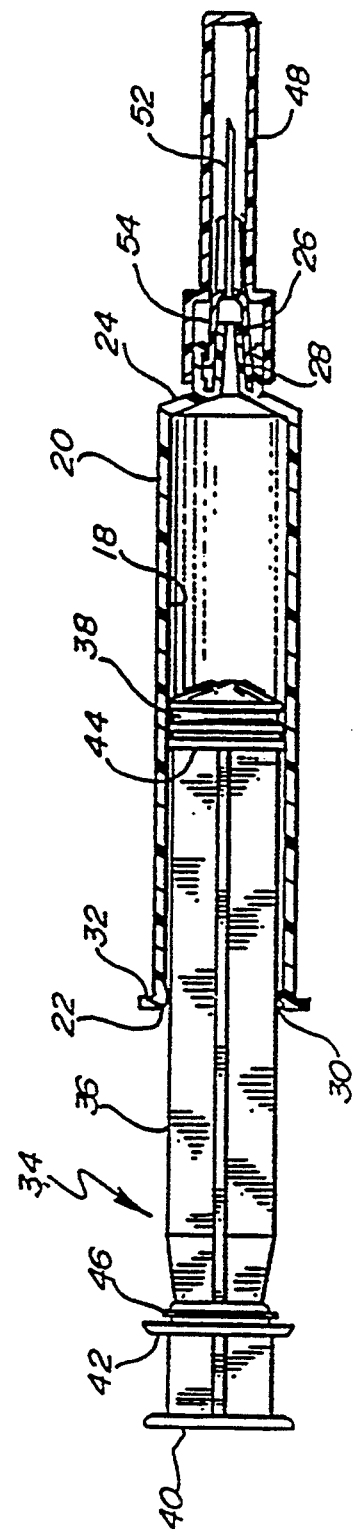

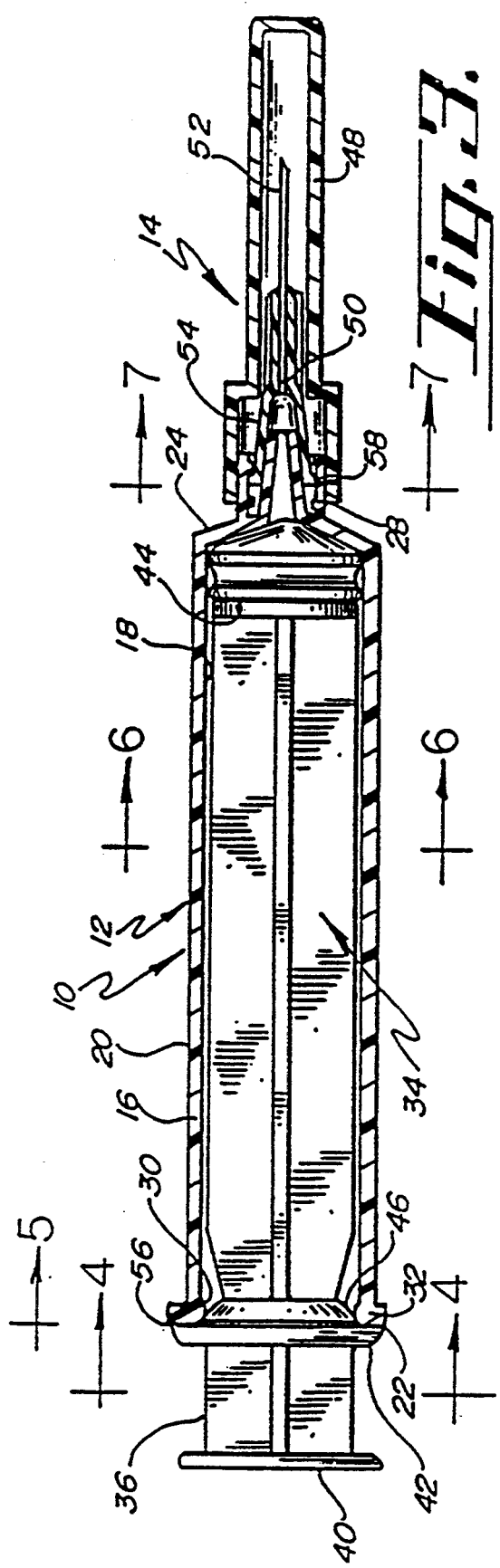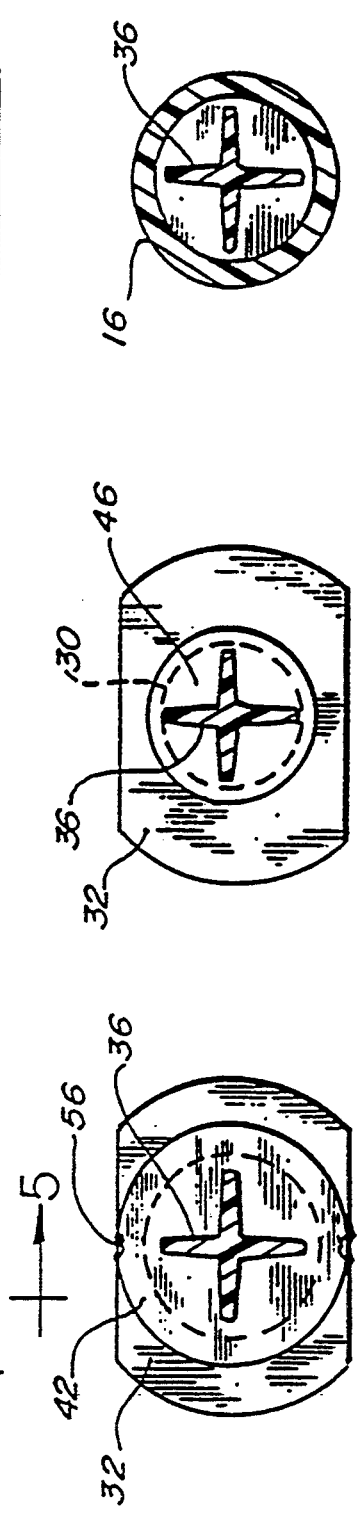

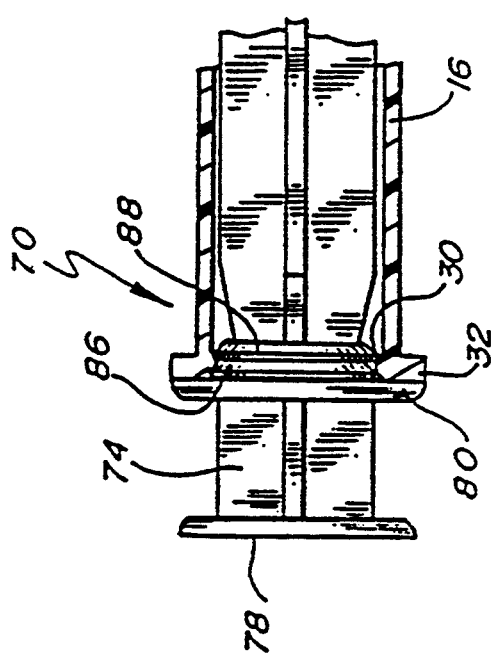
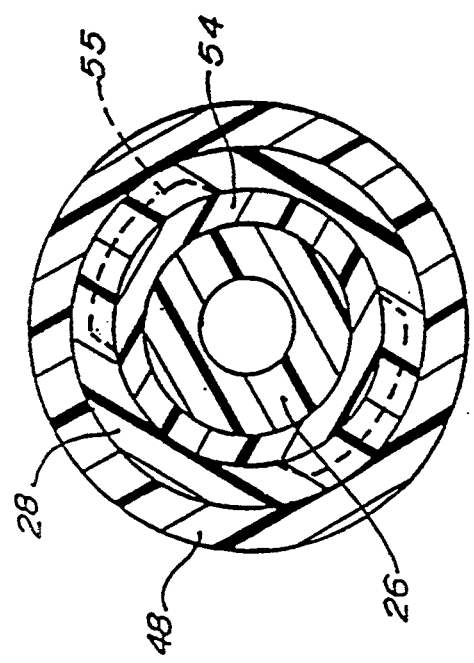
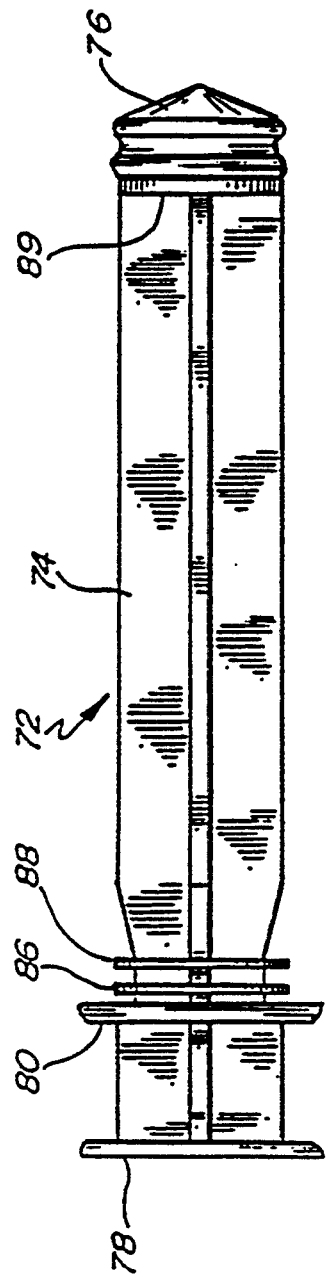

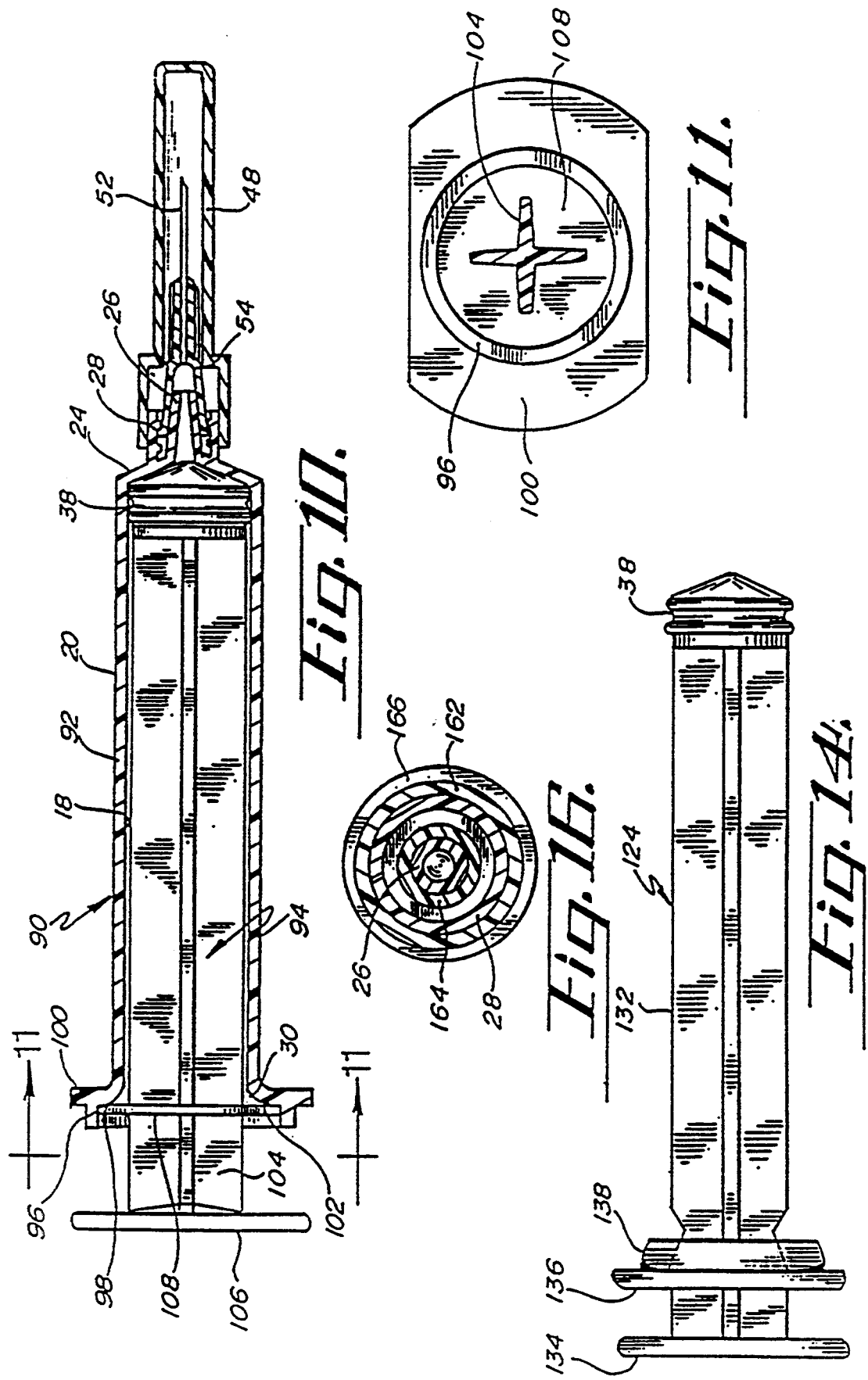

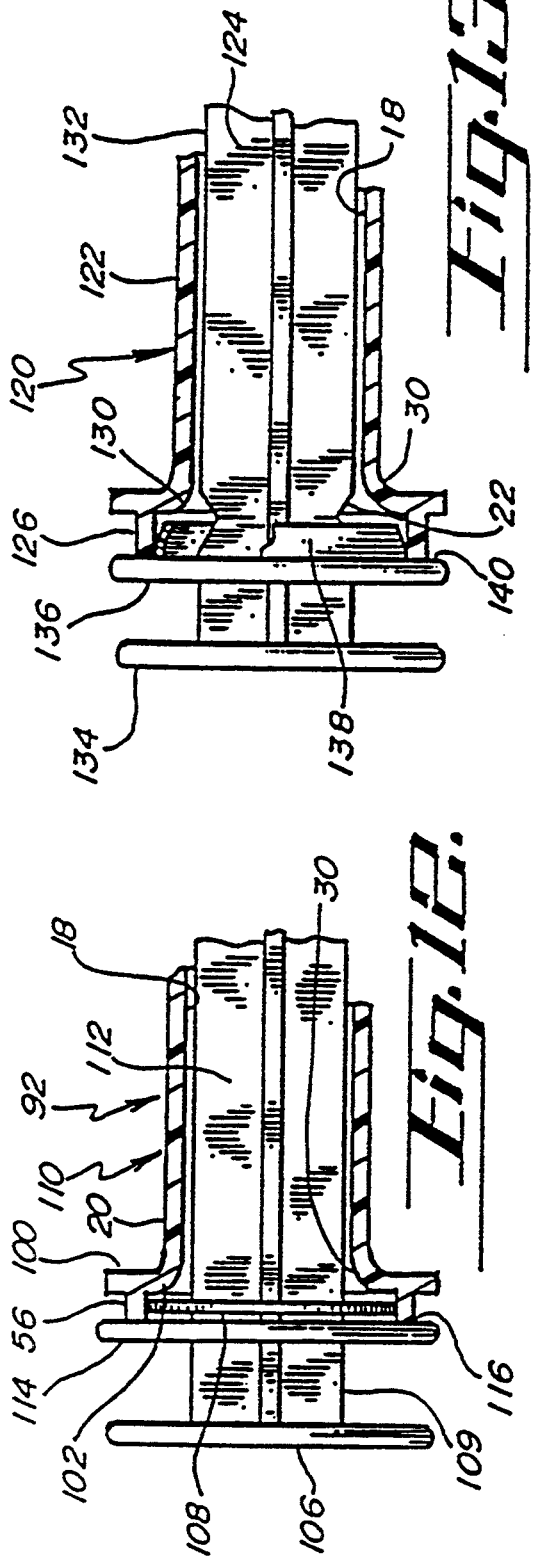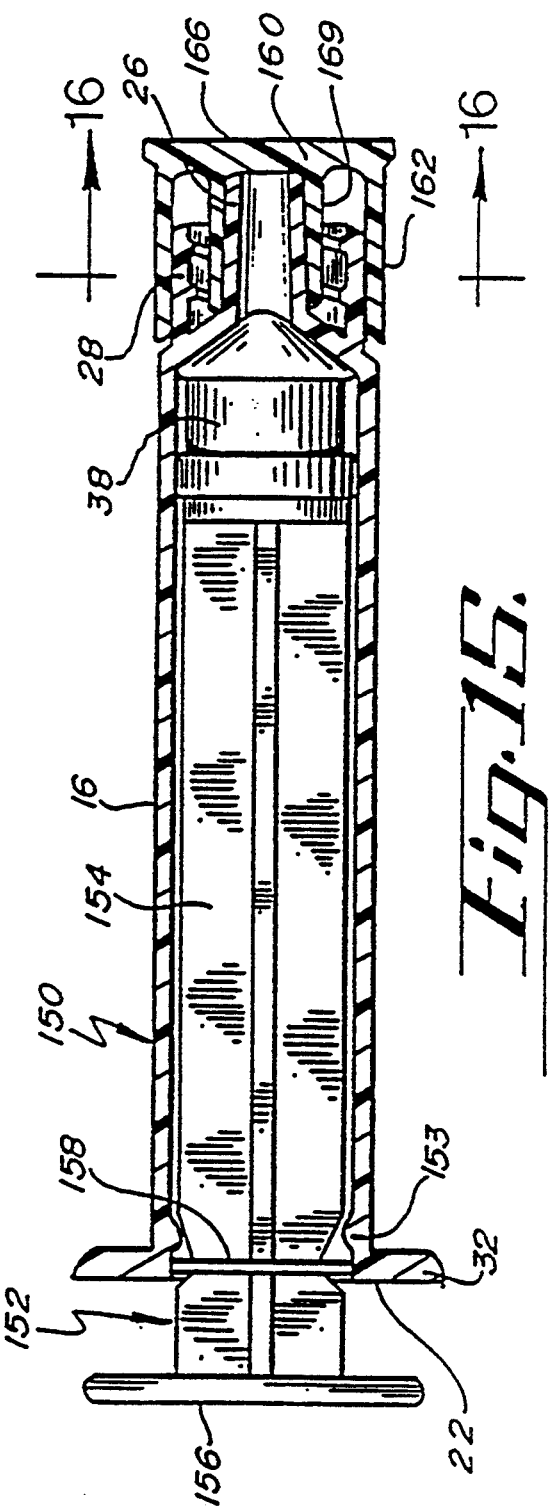

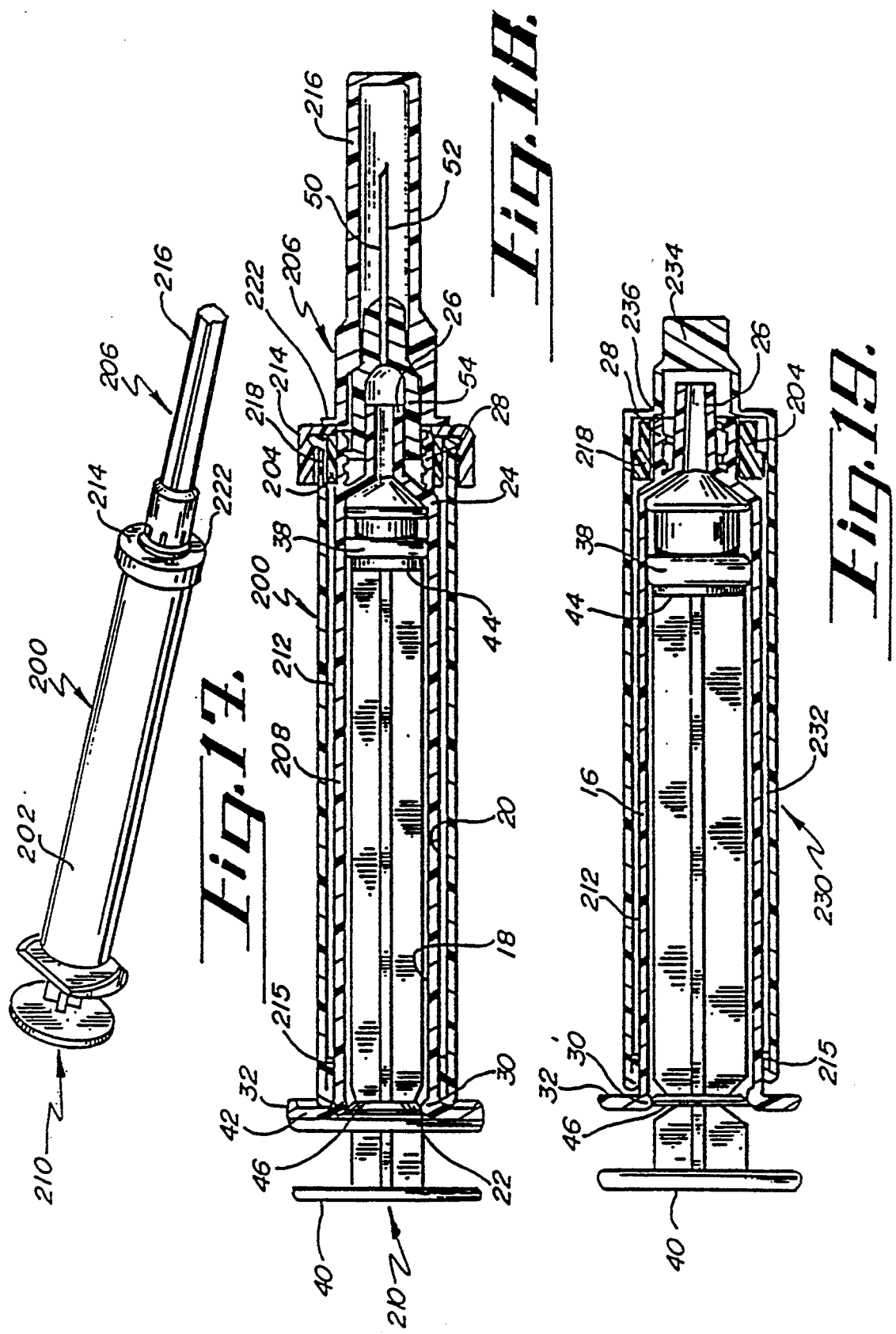

MEDICAL DEVICE WITH STERILE FLUID PATHWAY

FIELD OF THE INVENTION

This invention relates to medical devices which are provided in a sterile condition, and more particularly, to a syringe or similar device wherein the exterior of the device forms part of a barrier to protect the interior of the device from contamination prior to use.

BACKGROUND OF THE INVENTION

Medical devices which are usually provided in a sterile condition prior to use, are commonly protected during storage and handling by some form of packaging. This package typically includes one or more of the following desirable characteristics to maintain the sterility of the device prior to use. First, the packaging should effectively maintain the sterility of those elements of the device which will contact the patient, or which will be in contact with fluids to be administered to the patient. Second, the package should be "tamper-evident" or "use-evident" so that the user will be able to readily determine whether or not the sterility of the device may have been compromised prior to use. Third, the packaging should not impede the user's access to the device by requiring the disposal or removal of various components of the packaging prior to use. Fourth, the packaging should not require a modification of the conventional technique for Using the device. Fifth, the costs of manufacturing, shipping, storage and disposal of the device should be minimized by reducing the number and complexity of the components required for the packaged device. Finally, the packaging should provide adequate mechanical protection to ensure that the sterility of the device is maintained during shipping or storage.

In the prior art, one common method of packaging medical devices, such as syringes, has been to enclose the entire device in a sterile plastic or paper-type of package. U.S. Pat. No. 3,008,570 granted to Roehr et al. and U.S. Pat. No. 3,381,813 granted to Coanda et al. disclose packages wherein the entire syringe and needle or needle alone are fully enclosed within a plastic package. As disclosed in the Roehr et al. patent, the package preferably includes one or more frangible seals thereon to provide the user with an indication of when the package has been previously opened.

Another common approach to packaging syringes is to use the outer surface of the syringe barrel as part of the packaging. An early form of this approach is illustrated in U.S. Pat. No. 3,485,239 granted to Vanderbeck wherein an adhesive gas permeable wrap is positioned along the distal and proximal portions of the syringe assembly. A variation on this approach is disclosed in U.S. Pat. No. 4,300,678 granted to Gyure et al. wherein a cap member seals the proximal end of the syringe assembly and a frangible member, or a peelable section of material is used to seal the distal portion of the syringe assembly. Similarly, U.S. Pat. No. 3,828,775 granted to Armel discloses a device wherein a proximal cap encloses the proximal end of the syringe assembly and a frangible member encloses the distal end of the syringe barrel. A further variation on this approach is disclosed in U.S. Pat. No. 4,929,232 granted to Sweeney et al. wherein a cap member seals the proximal end of the syringe assembly and a securement collar is used to retain the needle shield on the distal end of the syringe barrel.

The packaging used in the above-described devices is believed to provide effective protection for the sterility of the syringes but they all fail to meet one or more of the desirable characteristics described above. One common deficiency of the above-described packaging occurs through the use of a cap or other member on the proximal end of the syringe assembly which must be discarded each time the syringe assembly is used. This is commonly considered to be nuisance trash because it is small and is usually left lying around the nurses station or other area where the device is opened. Similar complaints are found with packaging which includes a tearable or peelable seal to protect either the distal or proximal end of the syringe due to the need to discard the seal prior to Use of the syringe assembly.

Therefore, a need remains in the art for a package or device which satisfies all of the desirable characteristics described above without producing nuisance trash. As set forth more fully below, the present invention eliminates the need for a proximal end cap on the proximal end of the syringe barrel while providing an effective barrier which maintains the sterility of the interior surface of the syringe barrel prior to use. The barrier on the distal end of the present invention maintains the sterility of the distal portion of the syringe assembly and may take many forms as described more fully below depending on whether or not the device is packaged with a preattached needle.

SUMMARY OF THE PRESENT INVENTION

The medical devices with a sterile fluid pathway of the present invention preferably have a hollow body or syringe barrel for receiving a medical fluid therein. An operative element, such as a piston member, is movably disposed within the hollow body to control the flow of fluid into or from the hollow body. Means such as a plunger rod extends from the operative element outwardly through an opening in the hollow body for operatively moving the element and thereby controlling the flow of fluid into or from the hollow body. A preferably continuous member extends between the interior surface of the hollow body and the extending means to form a barrier at or adjacent to the proximal opening in the hollow body to prevent the entry of contaminates therethrough. Movement of the extending means causes the barrier to be broken and fluid may then be received within the hollow body or dispensed therefrom in a conventional manner.

In the first preferred embodiment of the present invention, the preferred form of the device is a syringe assembly consisting of a syringe and a needle assembly. The syringe preferably includes an elongate hollow tubular barrel defining an interior bore which is open to the outside at the breech or proximal end of the barrel. A plunger stop or lip member may extend radially inwardly along the proximal portion of the barrel generally at or adjacent to the opening at the proximal end thereof. A distal end wall on the barrel includes a reduced diameter portion which closes the distal end of the bore and has a fluid flow passage therethrough. The distal end of the barrel includes a tapered luer tip extending therefrom and a threaded cylindrical luer skirt surrounding the luer tip. A flexible piston member is positioned within the bore in slidable sealing engagement with the interior of the barrel, and a piston rod, connected to the piston member extends proximally and outwardly through the opening in the bore.

The plunger rod of the first preferred embodiment includes a distal end which is attached to the piston member and a proximal end which includes an enlarged first finger flange thereon. In this embodiment, a second enlarged flange is spaced distally along the plunger rod a short distance from the first finger flange. The second flange is positioned on the plunger rod such that when the piston member contacts the distal end wall of the barrel, the second flange contacts and substantially obstructs the proximal end of the barrel. The second flange is preferably heat staked to the proximal end of the barrel to provide a tamper-evident indicator therebetween. The plunger rod of this embodiment also includes a flexible disc member which extends radially outwardly therefrom. The flexible disc member is spaced apart from the distal side of the second flange on a reduced diameter portion of the plunger rod so that when the second flange contacts the proximal end of the barrel, the flexible disc member is flexed by the plunger stop or lip member on the interior surface of the barrel and a barrier is formed therebetween to prevent the contamination of the interior surface of the barrel through the proximal end.

The needle assembly of the first preferred embodiment preferably includes an elongate needle with a cannula having a sharpened distal tip on the distal end of the cannula and a needle hub on the proximal end of the cannula. An elongate needle sheath encloses the cannula and substantially encloses the needle hub. In the preferred embodiment, the needle sheath includes an enlarged and cylindrically shaped proximal portion which is designed to contact the outer surface of the luer skirt to form a barrier therebetween. Preferably, a heat stake is used to secure the proximal portion of the needle sheath to the luer skirt to provide a tamper-evident indicator to indicate when the needle sheath has been previously removed from the barrel.

With the first preferred embodiment of the present invention, the sterility of the interior surface of the barrel member, the cannula and portions of the needle hub is maintained by the barriers formed at the distal and proximal ends of the device. The proximal barrier is formed by the contact between the flexible disc member and the lip member on the interior surface of the proximal portion of the barrel and by contact between the second flange and proximal end of the barrel. The distal barrier is formed by contact between the proximal portion of the needle sheath and the outer surface of the luer skirt and by contact between the inner surface of the needle sheath and the distal portion of the needle hub and also by contact between the inner surface of the needle hub and the luer tip of the barrel as described more fully hereinafter.

In the remaining embodiments of the present invention, variations on the design of the distal and proximal barriers are disclosed. In the second preferred embodiment, the proximal end of the plunger rod is modified to include a pair of spaced apart flexible disc members thereon. In this embodiment, the flexible disc members are preferably positioned on the plunger rod such that when the piston member contacts the distal end wall of the barrel, the flexible disc members are deformed by the distal and proximal surfaces of the lip member on the interior surface of the proximal portion of the barrel to form a proximal barrier therebetween.

In the third and fourth preferred embodiments, the proximal end of the barrel is modified to include a proximally extending circumferential surface which is contacted by a modified flexible disc member on the plunger rod to form the proximal barrier. In the fifth preferred embodiment of the present invention, the proximal barrier is formed by a flexible member which extends distally from the distal side of the second flange. The flexible member contacts a proximally extending circumferential surface which extends from the proximal end of the barrel. The flexible member is formed such that when the piston member contacts the distal end wall of the barrel, the flexible member is deformed by the circumferential surface on the proximal end of the barrel. In the sixth preferred embodiment, a distal barrier is disclosed which may be used on devices wherein it is desirable not to include a needle assembly thereon.

In the final two preferred embodiments, the use of the distal and proximal barriers on safety syringe assemblies having slidable shields thereon is disclosed. In these embodiments, the distal barrier is formed preferably with a frangible member along the distal end of the shield.

BRIEF DESCRIPTION OF THE DRAWINGS

FIG. 1 is an exploded perspective view showing the syringe assembly of the first preferred embodiment of the present invention;

FIG. 2 is an assembled cross-section view taken longitudinally along the syringe assembly shown in FIG. 1 with the plunger rod assembly partially withdrawn from the barrel;

FIG. 3 is an assembled cross-sectional view taken longitudinally along the syringe assembly shown in FIG. 1 with the piston member of the plunger rod assembly positioned adjacent to the distal end wall of the barrel;

FIG. 4 is a cross-sectional view taken along lines 4—4 of FIG. 3;

FIG. 5 is a cross-sectional view taken along lines 5—5 of FIG. 3;

FIG. 6 is a cross-sectional view taken along line 6—6 of FIG. 3;

FIG. 7 is an enlarged cross-sectional view taken along lines 7—7 of FIG. 3;

FIG. 8 is a cross-sectional partial view showing the proximal portion of the syringe assembly of the second preferred embodiment of the present invention;

FIG. 9 is an elevated side view of the plunger rod assembly of the second preferred embodiment shown in FIG. 8;

FIG. 10 is a cross-sectional view showing the syringe assembly of the third preferred embodiment of the present invention;

FIG. 11 is cross-sectional view taken along lines 11—11 of FIG. 10 showing the syringe assembly of the third preferred embodiment of the present invention;

FIG. 12 is a cross-sectional partial view showing the proximal portion of the syringe assembly of the fourth preferred embodiment of the present invention;

FIG. 13 is a cross-sectional partial view showing the proximal portion of the syringe assembly of the fifth preferred embodiment of the present invention;

FIG. 14 is an elevated side view of the plunger rod assembly of the fifth preferred embodiment shown in FIG. 13;

FIG. 15 is a cross-sectional view showing the sixth preferred embodiment of the present invention for use on a syringe assembly without a needle assembly mounted thereon;

FIG. 16 is a cross-sectional view taken along lines 16—16 of FIG. 15;

FIG. 17 is a perspective view showing the syringe assembly of the seventh preferred embodiment of the present invention on a safety syringe having a protective shield which is movable between first and second positions wherein a needle is alternately exposed or protected;

FIG. 18 is cross-sectional view taken longitudinally along the seventh preferred embodiment shown in FIG. 17; and FIG. 19 is a cross-sectional view showing the syringe assembly of the eighth preferred embodiment of the present invention for use on a safety syringe having a protective shield which is movable between first and second positions wherein a needle assembly which is installed thereon prior to use is alternately exposed or protected.

DETAILED DESCRIPTION OF THE PREFERRED EMBODIMENTS

While this invention is satisfied by embodiments in many different forms, there is shown in the drawings and will hereinafter be described the presently preferred embodiments of the present invention. It should be understood that the present description is considered to be exemplary of the principles of the present invention and is not intended to limit the invention to the embodiments illustrated or described herein. The scope of the invention will be measured by the appended claims and their equivalents. For example, while the following description of the various embodiments of the present invention refer to a syringe assembly, it is anticipated that the present invention may be readily adapted for use on a number of different devices wherein it is desirable to maintain the sterility of the interior surface of the device prior to use.

For the purposes of the description of the present invention, the terms "distal" or "distal end" of an element is meant to refer to the portion or end of the element furthest from the person holding the device or syringe. The terms "proximal" or "proximal end" are used herein to refer to the portion or end of the element closest to the person holding the device or syringe.

As shown in FIGS. 1-7, the first preferred embodiment of the present invention consists of a syringe assembly 10, having sterility barriers and tamper-evident features. The syringe assembly 10 of this embodiment preferably includes a syringe 12 and a needle assembly 14. The syringe 12 includes an elongate and tubular or cylindrical barrel 16 having interior and exterior surfaces, 18 and 20 respectively, and an open breech or proximal end 22 and a reduced diameter distal end 24. A conically shaped luer tip 26 extends from the distal end 24 of the barrel 16 and includes a passageway therethrough in communication with the interior of the barrel 16. A cylindrically shaped luer skirt 28 also extends from the distal end 24 of the barrel 16. The luer skirt 28 is spaced apart from and generally encircles the luer tip 26 so that the needle assembly 14 may be attached thereto as described below. In this embodiment, the luer skirt 28 preferably includes a smooth outer surface and a plurality of threads on the inner surface thereof, the function of which are described more fully below. The proximal portion of the barrel 16 includes a plunger stop or lip member 30 which extends radially inwardly from the interior surface 18 of the barrel 16 near or at the proximal end 22 thereof. A generally oblong-shaped and outwardly extending finger flange 32 extends radially outwardly from the proximal end 22 of the barrel 16.

A plunger rod assembly 34 is slidably inserted through the open proximal end 22 of the barrel 16. The plunger rod assembly 34 preferably includes an elongate plunger rod 36 having distal and proximal ends and a piston member 38 mounted on the distal end thereof. The piston member 38 is preferably formed of a flexible and compressible material, such as butylrubber so that a fluid tight seal is formed between the interior surface 18 of the barrel 16 and the piston member 38. The plunger rod 36 is sized so that the proximal end of the plunger rod 36 extends proximally beyond the open proximal end 22 of the barrel 16 even when the piston member 38 is positioned adjacent to the distal end 24 of the barrel 16. As shown in FIGS. 4 and 6, the plunger rod 36 preferably has a generally X-shaped cross-section for the majority of the lengthwise dimension.

As shown best in FIGS. 2 and 3, the plunger rod 36 includes an enlarged first finger flange 40 on the proximal end thereof and an enlarged second flange 42 spaced a short distance distally therefrom. A smaller third flange-like member 44 is located along the proximal portion of the plunger rod 36 adjacent to the piston member 38. The third member 44 is preferably sized to provide a small amount of resistance as the third member 44 passes over the plunger stop or lip member 30 to provide an indication to the user that the plunger rod assembly 34 is about to be removed from the barrel 16 to prevent the inadvertent removal of the plunger rod from the barrel. Although the first and second flanges, 40 and 42, are preferably circularly shaped and have a circumference which is larger than the circumference of the interior surface 18 of the barrel 16 they may be oblong or otherwise shaped to assist the user in using the present invention. The diameter of the first flange 40 is preferably sufficient for the user to conveniently grasp the proximal end of the plunger rod assembly 34 to move the plunger rod assembly 34 proximally or distally in the barrel 16. The preferred diameter of the second flange 42 is approximately equal to or slightly greater than the diameter of the opening on the proximal end 22 of the barrel 16 or the smallest cross-sectional dimension of the finger flange 32 on the proximal end 22 of the barrel 16 and less than the largest cross-sectional dimension of the finger flange 32 on the barrel for the reasons described below.

A generally circularly-shaped flexible disc member 46 is also preferably located on the plunger rod 36. As shown in FIGS. 2 and 3, the disc member 46 is preferably spaced apart from the distal side of the second flange 42 at a reduced diameter portion of the plunger rod 36. The preferred circumference of the disc member 46 is approximately equal to the circumference of the interior surface 18 of the barrel 16 and greater than the circumference of the lip member 30 along the proximal portion of the barrel 16. As described more fully below, contact between the disc member 46 on the plunger rod 36 and the lip member 30 on the interior surface 18 of the barrel 16 preferably causes disc member 46 to flex against the lip member 30 to form a portion of the proximal barrier for the present embodiment.

As shown in the drawings, the present embodiment also includes a needle assembly 14 mounted on the distal end 24 of the syringe 12. The needle assembly 14 preferably includes an elongate needle sheath 48 and a needle 50 consisting of a cannula 52 and a needle hub 54. The cannula 52 includes a sharpened distal needle point thereon. As shown in FIGS. 2 and 3, the needle sheath 48 includes a distal portion which has a closed distal end to enclose and protect the needle 50. The proximal portion of the needle sheath 48 is generally cylindrically shaped and is sized to be slip fit around the outer surface of the luer skirt 28 to form a distal barrier therebetween. The distal portion of the needle hub 54 is sized to frictionally contact the interior surface of the needle sheath 48 adjacent to the intersection of the distal and proximal portions thereof to form a further distal barrier therebetween. Alternately, a rib (not shown) may be formed along the circumference of interior surface of the proximal portion of the needle sheath 48 to contact the needle hub 54 and form a distal barrier therebetween. A passageway extends through the needle 50 and needle hub 54 in communication with the passageway which extends through the luer tip 26 of the syringe 12 as described above. The interior surface of the needle hub 54 is sized to frictionally engage the outer surface of the luer tip 26 on the distal end 24 of the barrel 16 when the needle 50 is seated thereon to form a further distal barrier therebetween. The needle hub 54 also includes a plurality of outwardly extending ear members 55 thereon which engage the threads located on the interior surface of the luer skirt 28 as the needle 50 is threaded onto the distal end 24 of the barrel 16.

In the present embodiment, the primary distal barrier is preferably formed by the slip fit between the interior surface of the proximal portion of the needle sheath 48 and the exterior surface of the luer skirt 28. The distal barrier is secondarily formed by the contact between the distal portion of the needle hub 54 and the interior surface of the needle sheath 48 and the interior surface of the needle hub 54 and the exterior surface of the luer tip 26 on the barrel 16 as described above.

In order to provide a sterile syringe 12, there are two primary areas which must be protected against contamination. The first area is located distally of the piston member 38 and extends distally along the interior surface 18 of the barrel 16. This first area also includes the luer tip 26 on the barrel 16 and the needle 50 in the present embodiment. As described briefly above, the distal barrier in the present embodiment is formed primarily by the slip fit between the proximal portion of the needle sheath 48 and the outer surface of the luer skirt 28 and secondarily by the proximal portion of the needle hub 54 and distal end luer skirt 28 and the needle hub and luer tip 26 on the barrel 16 to maintain the sterility of the surfaces and portions of the syringe 12 that are located distally of the piston member 38 and which either contact the patient or contact fluids which may contact the patient.

The second area of the syringe 12 that must remain free of contamination is located along the interior surface 18 of the barrel 16 between the proximal end 22 of the barrel 16 and the piston member 38. It is important to maintain the sterility of this portion of the barrel 16 because if this portion of the barrel 16 is contaminated, any fluid that is to be injected into or withdrawn from the patient may contact the contaminated interior surface 18 of the barrel 16 when the plunger rod assembly 34 is withdrawn towards the proximal end 22 of the barrel 16. In the present embodiment, the proximal barrier is formed primarily by the contact between the disc member 46 on the plunger rod 36 and the lip member 30 on the interior surface 18 of the barrel 16, A secondary barrier is formed by the abutment of the distal surface of the second flange 42 against the proximal surface of the finger flange 32 at the proximal end 22 of the barrel 16.

In addition to maintaining the sterility of the syringe assembly 10 through the use of a minimum number of elements, the present embodiment also includes means for indicating whether or not the syringe assembly has been previously opened. These tamper-evident or use-evident elements enable the user to readily determine whether or not the sterility of the syringe assembly 10 may have been compromised prior to use. In the present embodiment, one or more heat stakes 56 are applied to the second flange 42 on the plunger rod 36 and the finger flange 32 on the barrel 16 to bond a portion of the second flange 42 to the finger flange 32. This heat stake 56, in addition to providing a tamper or use-evident indicator, also functions to ensure that the contact between the disc member 46 and the lip member 30 is maintained prior to the use of the syringe assembly 10.

The second means for indicating whether or not the syringe assembly 10 has been opened prior to use preferably consists of one or more heat stakes 58 which are applied to the proximal portion of the needle sheath 48 and the outer surface of the luer skirt 28 to bond a portion of the needle sheath 48 to the luer skirt 28. This heat stake 58, in addition to providing a tamper or use-evident indicator on the distal end of the syringe assembly 10, also functions to secure the needle sheath 48 to the luer skirt 28 prior to use. Although the preferred form of tamper-evident indicators is described herein as being heat stakes, other methods of fusing or joining the elements may be used. For example, it is anticipated that spin welding, laser welding, ultrasonic welding and other methods which are compatible with the polypropylene used in the syringe assembly 10 may be used. Alternately, various forms of tape or adhesives may be used to join the respective elements of the syringe assembly 10 together to provide a tamper-evident indicator thereon.

As described above and shown in FIG. 3, when the present embodiment is assembled for shipping and storage, the second flange 42 on the plunger rod 36 is heat staked to the finger flange 32 on the barrel 16. In this position, the disc member 46 is flexed against the lip member 30 and the piston member 38 is located adjacent to the distal end 24 of the interior surface 18 of the barrel 16. On the distal end of the syringe assembly 10, the proximal portion of the needle sheath 48 securely surrounds the luer skirt 28 and protects the needle 50 against potential contamination. The needle hub 54 is preferably positioned on the luer tip 26 of the barrel 16 and along the threads on the interior surface of the luer skirt 28 such that a small amount of proximal movement along the luer tip 26 and luer skirt 28 is possible. The needle 50 is maintained in this position prior to use by contact between the needle hub 54 and the intersection of the distal and proximal portions of the needle sheath 48 and the frictional contact between the ear members 55 on the needle hub 54 and the threads on the luer skirt 28. Therefore, the exterior surface of the needle sheath 48, the exterior surface 20 of the barrel 16 and the flexible disc member 46 and lip member 30 form an overall barrier which maintains the sterility of the components of the syringe assembly 10 which may contact the patient either directly or indirectly and also provide an indication of when the sterility of the device may have been compromised prior to use.

The use of the present embodiment requires little or no substantive modification of the conventional technique for using a syringe. When the user desires to use the present embodiment, the heat stake 58 on the distal end of the syringe assembly 10 is preferably broken first by grasping the barrel 16 with one hand while twisting the needle assembly 14 in a clockwise manner. This rotation of the needle assembly 14 causes the outwardly extending ear members 55 on the needle hub 54 to be fully seated in the threads on the interior surface of the luer skirt 28 and also causes the interior surface of the needle hub 54 to fully engage the outer surface of the luer tip 26 on the barrel 16. Next, the needle sheath 48 may be removed to expose the needle 50. If the user inadvertently rotates the needle assembly 14 in a counter-clockwise manner, the needle assembly 14 may be reattached to the distal end 24 of the barrel 16 by merely aligning the distal end 24 of the barrel 16 with the needle hub 54 and rotating the needle assembly 14 in a clockwise manner. This same procedure may be used if the user desires to mount a different needle on the syringe 12 prior to the use of the syringe assembly. Finally, the barrel 16 of the syringe assembly 10 is grasped in one hand while the user grasps and twists the plunger rod 36 adjacent to the first flange 40. This breaks the heat stake 56 between the second flange 42 on the plunger rod 36 and the finger flange 32 on the barrel 16. Once this heat stake 56 is broken, the sterility of the interior surface 18 of the barrel 16 will be maintained as long as the contact between the disc member 46 and the lip member 30 is maintained. Alternately, it is anticipated that the user may break the proximal heat stake 56 first and then break the distal heat stake 58 and remove the needle sheath from the syringe assembly 10 immediately prior to use.

The second preferred embodiment of the present invention is shown in FIGS. 8 and 9 where like numbers have been added to like elements as set forth above. For the sake of brevity and clarity, the description of the elements of the present embodiment will not be repeated herein except as is believed to be necessary for an understanding of the differences between the respective preferred embodiments. Reference should be made to the foregoing description and drawings of the first preferred embodiment for an understanding of the elements which are common to the respective preferred embodiments.

The syringe assembly 70 of the second preferred embodiment includes a syringe 12 having a barrel 16 of the type described above and a needle assembly 14 of the type described above. As shown in FIGS. 8 and 9, a modified plunger rod assembly 72 is used with the present embodiment. The plunger rod assembly 72 of this embodiment includes an elongate plunger rod 74 having distal and proximal ends and a piston member 76 mounted on the distal end thereof. As shown in FIG. 8, the plunger rod 74 extends distally from the piston member to a location proximally of the open proximal end 22 of the barrel 16. The plunger rod 74 includes an enlarged first finger flange 78 on the proximal end thereof and an enlarged second flange 80 spaced apart from the first flange 78 distally along the plunger rod 74. The first and second flanges, 78 and 80, are sized and shaped to be conveniently grasped by the user and include a circumference which is larger than the circumference of the open proximal end 22 of the barrel 16. This second flange 80 is also sized and shaped to be conveniently heat staked 82 to the finger flange 32 located on the proximal end 22 of the barrel 16. The plunger rod 74 also includes a third flange-like member 84 located along the distal portion of the plunger rod 74 and adjacent to the proximal side of the piston member 76. The third flange 84 is sized to fit within the barrel 16 and functions as a plunger stop when the plunger rod 74 is withdrawn from the barrel 16 by contacting the lip member 30 on the interior surface 18 of the barrel 16 to provide an indication to the user that the plunger rod 74 is about to be withdrawn from the barrel 16.

As shown in FIGS. 8 and 9, the plunger rod 74 of the second preferred embodiment also includes first and second flexible disc members, 86 and 88 respectively, thereon. The disc members, 86 and 88, are preferably spaced apart from the distal side of the second flange 80 distally along the plunger rod 74. As with the first preferred embodiment, the cross-sectional diameter of the plunger rod 74 is reduced at the location where the disc members, 86 and 88, extend radially outwardly from the plunger rod 74 thereby increasing the flexibility of the disc members 86 and 88. The disc members 86 and 88 are spaced apart from each other a sufficient distance so that when the plunger rod 74 is fully inserted into the barrel 16, the first disc member 86 will preferably flex against the proximal side of the lip member 30 and the second disc member 88 will preferably flex against the distal side of the lip member 30 as shown in FIG. 8 to form a proximal barrier therebetween. The use of the second disc member 88 in this embodiment provides a further barrier to protect the sterility of the interior surface 18 of the barrier 16 and may also be used in devices, such as many syringe assemblies, where the length of the barrel 16, plunger rod 74 or piston member 76 may vary slightly due to manufacturing tolerances or other manufacturing concerns. In these devices, the use of the first and second disc members 86 and 88, will ensure that at least one of the disc members will form an effective barrier with either the interior surface 18 of the barrel 16 or the lip member 30 on the barrel 16.

FIGS. 10–12 show the third and fourth preferred embodiments of the present invention. As with the second preferred embodiment, like numbers have been added to like elements as more fully described above in the description and drawings of the first preferred embodiment. For the sake of brevity and clarity, the description of the elements of the present embodiments which are similar to the elements of the first preferred embodiment will not be repeated herein except as is believed to be necessary for an understanding of the differences between the respective preferred embodiments. Reference should be made to the foregoing description and drawings of the first preferred embodiment for an understanding of the elements which are common to the respective preferred embodiments.

As shown in FIG. 10, the distal barrier of the syringe assembly 90 of the third preferred embodiment is similar to that of the distal barrier described above with respect to the first preferred embodiment of the present invention. In the present embodiment, the principles of the present invention are applied to a modified barrel 92 and plunger rod assembly 94. As shown in FIGS. 10 and 11, the barrel 92 of the present embodiment includes a cylindrically shaped and proximally extending extension 96 on the proximal end 22 thereof. Although the diameter of the extension 96 is preferably greater than the diameter of the barrel 92, the diameter of the extension 96 and barrel 92 may be equal without materially affecting the function of the present embodiment. As shown in FIG. 11,, the extension 96 is preferably sized and shaped to surround the open proximal end 98 of the barrel 92. The intersection of the extension 96 and the interior portion of the finger flange 100 on the barrel 92 form a rim-like surface 102 therebetween.

The plunger rod assembly 94 of the third preferred embodiment includes a piston member 38 of the type described above and a modified plunger rod 104. The plunger rod 104 preferably includes an enlarged first finger flange 106 on the proximal end thereof which is sized and shaped to enable the user to conveniently grasp the proximal portion of the plunger rod 104. An enlarged disc member 108 is located on the plunger rod 104 distally of and spaced apart from the first flange 106. In this third preferred embodiment, the disc member 108 extends radially outwardly from the plunger rod 104 a greater distance than the disc members of the prior preferred embodiments. The disc member 108 of this embodiment is positioned along the proximal portion of the plunger rod 104 so that when the piston member 38 is located against the distal end 24 of the barrel 16, the disc member 108 will be positioned in the interior of the extension 96 on the barrel 92, thereby forming a barrier with the interior surface of the extension 96 by obstructing the access of contaminates into the open proximal end 98 of the barrel 92. In this embodiment, it may be preferable to heat stake or otherwise affix the disc member 108 or plunger rod 104 to a portion of the barrel 92 or extension 96 to maintain the barrier between the disc member 108 and the extension 96 prior to use of the syringe assembly 90. This embodiment is also particularly useful where the lengths of the barrel 92 or plunger rod assembly 94 may vary due to manufacturing tolerances or other manufacturing concerns.

As shown in FIG. 12, the fourth preferred embodiment of the present invention is similar to the third preferred embodiment described above. The fourth preferred embodiment includes a syringe assembly 110 having a further modification to the plunger rod 112. The plunger rod 112 of this embodiment includes a second flange 114 having a circumference which is approximately equal to or slightly greater than the outer circumference of the extension 96 on the barrel 92. The second flange 114 is spaced apart from the first flange 106 distally along the plunger rod, 112 such that when the piston member 38 is positioned adjacent to the distal end 24 of the barrel 92, the second flange abuts against the proximal side of the extension 96 and the disc member 108 is flexed against the interior surface of the extension 96. In this embodiment, the second flange 114 may be heat staked 116 or otherwise affixed to the proximal side of the extension 96.

The second flange 114 performs three important functions in the present embodiment. The first function of the second flange 114 in this embodiment relates to the use of the heat stake 116 to provide a readily observable means for determining whether or not the sterility of the device may have been compromised prior to use. The second function of the second flange 114 is to maintain the contact between the disc member 108 and the interior surface of the extension 96 while the heat stake 116 between the second flange 114 and the extension 96 is intact. The third function of the second flange 114 is to form a further barrier between the outer surface of the syringe assembly and the interior surface 18 of the barrel 92. A part of the third function of the second flange 114 in this embodiment, and the other embodiments of the present invention, may be due at least partially to the perception of many users that a solid member must physically block the open proximal end 22 of the barrel 92 to maintain the sterility of the syringe assembly 110. This is important because if the user does not believe that the device is sterile, they will not use it.

FIGS. 13 and 14 show the fifth preferred embodiment of a syringe assembly 120 of the present invention where like numbers have been added to like elements. As with the preferred embodiments described above, the following description of the present embodiment will not repeat the description of the elements described and shown above in the description and drawings of the first preferred embodiment except as is believed to be necessary for an understanding of the differences between the first preferred embodiment and the present embodiment. Reference should be made to the foregoing description and drawings of the first preferred embodiment for an understanding of the elements which are common to the respective preferred embodiments.

The syringe assembly 120 of the present embodiment preferably includes a distal barrier similar to that of the distal barrier described above with respect to the first preferred embodiment and shown in FIGS. 1-3. In the present embodiment, the principles of the present invention are applied to a modified barrel 122 and plunger rod assembly 124. The barrel 122 of the present embodiment includes a cylindrically shaped and proximally extending barrel extension 126 on the proximal end 22 thereof similar to the extension 96 described above with respect to the third and fourth preferred embodiments. The barrel extension 126 is preferably circularly shaped and includes an inner circumference that is greater than the inner circumference of the interior surface 18 of the barrel 122 such that a rim-like member 130 is formed therebetween. For the reasons described below, it is anticipated that the interior or exterior surfaces of the barrel extension 126 may be either parallel to or tapered with respect to the longitudinal axis of the syringe assembly 120.

The plunger rod assembly of the fifth embodiment includes an elongate plunger rod 132 and a piston member 38. The plunger rod 132 includes the piston member 38 mounted on the distal end thereof and an enlarged and preferably circular first flange 134 on the proximal end thereof. An enlarged second flange 136 is spaced apart from the first flange 134 distally along the plunger rod 132. As shown in FIGS. 13 and 14, the second flange 136 includes a distally extending ring-like rod extension 138 which projects from the periphery of the distal-side of the second flange 136. In this embodiment, the ring-like rod extension 138 is preferably a flexible member which forms a barrier with the interior surface of the barrel extension 126. As briefly described above, the outer surface of the ring-like rod extension 138 may be tapered inwardly or otherwise shaped to matingly fit with the interior surface of the barrel extension 126 to form a proximal barrier therebetween. Alternately, the exterior surface of the barrel extension 126 may be tapered such that the interior surface of the ring-like rod extension 138 contacts the exterior surface of the barrel extension 126 to form a proximal barrier therebetween. The second flange 136 of this embodiment may also be heat staked 140 to the barrel extension 126 to form a means for detecting when the sterility of the syringe assembly 120 may have been compromised prior to use. Although not shown in the drawings, it is also anticipated that the second flange 136 and the ring-like rod extension 138 may be sized to fit adjacent to the rim-like member 130 of the barrel 122 such that a proximal barrier is formed between the ring like extension 138 and the interior surface 18 or lip member 30 of the barrel 122. In this form of the fifth preferred embodiment, the second flange 136 may be heat staked to the rim-like member 130 or a further flange may be added to the plunger rod 132 so that the further flange may be heat staked to the proximal side of the barrel extension 126 on the barrel 122.

FIGS. 15 and 16 show the sixth preferred embodiment of the present invention. As with the prior preferred embodiments, like numbers have been added to like elements as more fully described above in the description and drawings of the first preferred embodiment. For the sake of brevity and clarity, the description of the elements of the present embodiment which are similar to the elements of the first preferred embodiment will not be repeated herein except as is believed necessary for an understanding of the differences between the respective preferred embodiments. Reference should be made to the foregoing description and drawings of the first preferred embodiment for an understanding of the elements which are common to the respective preferred embodiments.

As shown in FIGS. 15 and 16, the principles of the present invention are shown on a modified syringe assembly 150. In this embodiment, the barrel 16 of the device remains substantially unchanged while the proximal and distal barriers are simplified. As shown in FIG. 15, the lip member 153 on the interior surface 18 of the barrel 16 is spaced apart distally from the proximal end 22 of the barrel 16 and the plunger rod assembly 152 includes a modified plunger rod 154 with a piston member 38 mounted on the distal end thereof. The proximal portion of the plunger rod 154 includes a single enlarged flange 156 on the proximal end thereof and a flexible disc member 158 spaced apart from the flange 156 distally along the plunger rod 154. When the piston member 38 is positioned adjacent to the distal end 24 of the barrel 16, the disc member 158 is flexed against the interior surface 18 of the barrel 16 to form the proximal barrier of the syringe assembly 150. In this embodiment, the lip member 153 functions as a plunger stop to prevent the inadvertent withdrawal of the plunger rod assembly 152 from the barrel 16.

As shown in FIGS. 15 and 16, the distal end 24 of the barrel 16 includes the luer tip 26 and luer skirt 28 as described more fully above with respect to the first preferred embodiment. A syringe cap 160 is mounted on the distal end of the barrel 16. The syringe cap 160 includes an outer first circular portion 162 which contacts and engages the outer-surface of the luer skirt 28. An inner second circular portion 164 is positioned inwardly of the first circular portion 162. The second circular portion 164 contacts and engages the outer surface of the luer tip 26 on the distal end of the barrel 16. The distal end of the syringe cap 160 includes an enlarged end member 166 which closes the end of the syringe cap 160. Therefore, the distal barrier of the syringe assembly 150 of the present embodiment is formed by the contact between the first circular portion 162 and the luer skirt 28 and also by the contact between the second circular portion 164 and the luer tip 26 on the distal end of the barrel 16. It is anticipated that the first circular portion 162 will be heat staked 168 or otherwise affixed to the outer surface of the luer skirt 28 to provide an indication to the user that the sterility of the distal end of the syringe assembly 150 may have been compromised prior to use. Alternately, if the syringe cap 160 is used on a device having elongate ribs on the exterior surface of the luer skirt 28, the first circular portion 162 will function basically as a dust cover while the primary distal barrier will be formed by contact between the second circular portion 162 and the luer tip 26.

FIGS. 17-19 show the final two preferred embodiments of the present invention wherein the principles of the present invention are applied to safety syringes which include a shield movably mounted about the barrel such that the shield is movable between a first position wherein the needle may be exposed and a second position wherein the needle is protected by the shield. Although the safety syringes shown in FIGS. 17-19 are preferably of the type shown in U.S. Pat. No. 5,053,018 (which is incorporated herein by reference), it is anticipated that the principles of the present invention may be applied to nearly any safety syringe having a movable shield to provide a sterile self contained syringe assembly.

As with the preferred embodiments described above, in the following description of the seventh and eighth preferred embodiments like numbers have been added to like elements. Additionally, the description of the present embodiments will not repeat the description of the elements described above in the description of the first preferred embodiment except as is believed to be necessary for an understanding of the present embodiment. Reference should be made to the foregoing description and drawings of the first preferred embodiment for an understanding of the elements which are common to the present preferred embodiments.

As shown in FIGS. 17 and 18, the seventh preferred embodiment includes a syringe assembly 200 having a shield 202 and collar 204 thereon and a needle assembly 206. In this embodiment, the preferred form of the barrel 208 and plunger rod assembly 210 are substantially identical to the barrel 16 and plunger rod assembly 34 described above with respect to the first preferred embodiment and therefore, these elements will not be thoroughly discussed herein.

The shield 202 of the present embodiment is preferably an elongate and tubular member having generally open proximal and distal ends. The shield 202 preferably includes one or more keys 212 which extend inwardly and longitudinally between the proximal and distal ends of the shield 202. The distal end of the shield 202 includes an end cap 214 as shown in cross-section in FIG. 18 and the proximal end of the shield 202 preferably includes a reduced diameter portion 215 thereon. The end cap 214 is preferably rotatably mounted to the distal end of the shield 202 and includes an opening therein which is sized to allow the needle 50 of the needle assembly 206 from passing therethrough while preventing the needle sheath 216 from passing therethrough as described more fully below.

The collar 204 of the present embodiment is fixedly mounted on the outer surface of the luer skirt 28. The outer surface of the collar 204 preferably includes a plurality of longitudinally aligned and recessed keyways 218 thereon. The keyways 218 are sized to receive the keys 212 therein as the shield 202 is moved between the retracted and extended positions as described more fully below. The collar 204 also preferably includes a plurality of locking slots (not shown) on the distal portion of the collar 204. The locking slots are shaped to receive the proximal ends of the keys 212 therein when the shield 202 is rotated from a releasable extended position to a locked and extended position as described more fully in U.S. Pat. No. 5,053,018.

The needle assembly 206 of the present embodiment includes a needle 50 as described above with respect to the first preferred embodiment and an elongate needle sheath 216. The needle sheath 216 includes a distal portion having a closed distal end thereon and a proximal portion which includes an enlarged diameter and a generally cylindrical shape. The interior of the intersection between the proximal portion and the distal portion is sized so that the distal portion of the needle hub 54 will contact and engage the intersection. As shown in FIGS. 17 and 18, the proximal end of the needle sheath 216 preferably includes a scored sheath break ring 222 thereon. The break ring 222 preferably extends around the circumference of the proximal end of the needle sheath 216 and is welded, heat staked or otherwise affixed to the end cap 214 on the distal end of the shield 202.

In the seventh preferred embodiment, the proximal barrier is formed primarily by contact between the disc member 46 on the plunger rod assembly 210 and the lip member 30 on the interior surface 18 of the barrel 208 and secondarily by contact between the second flange 42 on the plunger rod assembly 210 and the proximal side of the finger flange 32 on the barrel 208. As With the first preferred embodiment, the second flange 42 may be heat staked or otherwise affixed to the finger flange 32 to provide an indicator to identify whether or not the sterility of the interior surface 18 of the barrel 208 may have been compromised prior to use.

Unlike the first preferred embodiment, the distal barrier in the present embodiment is formed by the contact between the break ring 222 and proximal end of the needle sheath 216 with the distal side of the end cap 214 on the shield 202. A secondary barrier is also formed by contact between the needle hub 54 and needle sheath 216 and by the needle hub 54 and luer tip 26 on the distal end of the barrel 208.

A further barrier is preferably formed between the exterior surface 20 of the barrel 208 and the interior surface of the shield 202. This additional barrier is desirable to maintain the sterility Of the exterior surface 20 of the barrel 208 and the interior surface of shield 208 prior to use. If this barrier is not present, the interior surface of the shield 208 may compromise the sterility of the needle 50 prior to use. In this embodiment, the barrier is formed along the proximal portion of the barrel 208 by contact between the reduced diameter portion 215 of the shield 202 and the exterior surface 20 of the barrel 208. The reduced diameter portion 215 of the shield 202 in this embodiment is preferably formed by folding over the proximal end of the shield 202 during manufacture of the device. A heat stake or other tamper-evident indicator may be used in this embodiment to signal to the user that the shield 202 may have been moved to the extended position prior to use, thereby compromising the sterility of the needle 50. Although not shown in the drawings, a heat stake may be applied to the proximal end of the shield 202 and the barrel 208 or to the shield 202 and the finger flange 32 on the barrel 208 to provide a tamper-evident indicator to detect when this barrier may have been compromised prior to use. The inner diameter of the reduced diameter portion 215 is sized to contact the exterior surface 20 of the barrel 208 immediately distal of the finger flange 32. When the shield 202 is moved to the extended position, the reduced diameter portion 215 is spaced apart from the exterior surface 20 of the barrel 108 at the distal end 24 thereof because the barrel 208 has a larger diameter at the proximal end 22 than the distal end 24 because of the molding processes used to manufacture the barrel 208.

When the user desires to use the syringe assembly 200 of the present embodiment, the needle sheath 216 is initially twisted clockwise about the barrel 208 to fully seat the needle hub 54 on the luer tip 26 of the barrel 208. In this embodiment, when the needle sheath 216 is rotated, the end cap 214 is also rotated so that the break ring 222 remains intact until the shield 202 is moved to the extended position as described below. The shield 202 is then moved to an extended position wherein the keys 212 are slid distally in the keyways 218 on the collar 204 until the distal end of the shield 202 projects beyond the distal end of the needle 50 and the proximal end of the shield is adjacent to the distal end 24 of the barrel 208. The needle shield 202 and collar 204 of this embodiment preferably include an indicating means such as the reduced diameter portion 215 on the proximal end of the shield 202 to indicate to the user when the shield 202 has reached the fully extended position. Additionally, the indicating means preferably provides a slight resistance to the proximal movement of the shield 202 to retain the shield 202 in the extended position once the shield 202 has reached the fully extended position. The needle sheath 216 is snapped or twisted off the distal end of the shield to remove the connections between the proximal end of the needle sheath 216 and the break ring 222. Next, the shield 202 is moved distally along the barrel 208 to the retracted position wherein the cannula 52 of the needle 50 is exposed and extends through the opening in the end cap 214 on the shield 202. Next, the plunger rod assembly 210 is twisted with respect to the barrel 208 and shield 202 to break the heat stake between the second flange 42 on the plunger rod assembly 210 and the finger flange 32 on the barrel 208. The user may then draw medication into the syringe assembly 200 in the conventional manner. Optionally, the user may now move the shield 202 to the extended position before the syringe assembly 200 is transported to the bedside, and then retract the shield 202 prior to use. Once the injection has been made, the user may slide the shield 202 distally along the barrel 208 to the extended position. With the present embodiment, the user may then rotate the shield 202 about the barrel 208 to lock the keys 212 into the locking slots on the collar 204 thereby locking the shield 202 in the extended position. With this method of using the present embodiment, the user is able to use the syringe assembly in a conventional manner while protecting themselves and others from accidental contact with the needle.

FIG. 19 shows the eighth preferred embodiment of the present invention wherein the safety syringe shown in FIGS. 17 and 18 is modified for use in a syringe assembly 230 which does not includes a needle assembly as described above. In this embodiment, the shield 232 is preferably a molded one-piece member and the distal end of the shield 232 is modified to include a frangible distal cap 234 thereon. The distal cap 234 is retained on the distal end of the shield 232 until the user removes the distal cap 234 from the shield 232 by twisting, pulling or pushing the distal cap 234 with respect to the shield 232 to rupture a frangible portion 236 which is preferably located along the periphery of the distal cap 234. Once the distal cap 234 is removed, the user may attach a conventional needle assembly to the luer skirt 28 and luer tip 26 of the barrel 208 in a conventional manner. Preferably, the opening formed on the distal end of the shield 232 is sized such that a needle hub of the needle assembly will extend through the opening while the needle sheath is prevented from extending therethrough. The user may then use the syringe assembly 230 of the present embodiment in the manner described above with respect to the seventh preferred embodiment.

The foregoing represents a detailed description of the presently preferred embodiments of the present invention. It is anticipated that various combinations of the distal and proximal barriers as disclosed above may be interchanged or modified without departing from the scope of the present invention which is defined by the following claims.

What is claimed is:

1. A medical device comprising:
   an elongate and tubular syringe barrel having interior and exterior surfaces and distal and proximal ends, the interior surface having a radially inwardly extending member positioned adjacent its proximal end;
   piston means disposed in said body member for controlling the flow of fluid into and out of said body member, said piston means being movable from a first position blocking the flow of fluid into and out of said body member to a second position allowing the flow of fluid into and out of said body member;
   a plunger rod having distal and proximal ends wherein said distal end is operatively connected to said piston means and said proximal end is disposed to extend proximally from said proximal end of said body member, said plunger rod being movable with said piston means, the plunger rod having a radially extending flexible disc member thereon such that said radially inwardly extending lip member of the syringe barrel is sealingly engaged by said flexible disc member to form a proximal barrier when said piston means is in said first position to prevent the contamination of said interior surface of said syringe barrel through the proximal end of said syringe barrel.

2. The medical device of claim 1 wherein said plunger rod includes a flange member thereon which substantially blocks said proximal end of said barrel when said piston means is adjacent to said distal end of said barrel.

3. The medical device of claim 1 wherein a distal barrier is formed between said distal end of said barrel and a member which is removably mounted adjacent said distal end of said barrel.

4. A medical device comprising:
   an elongate and tubular barrel member having distal and proximal ends and an interior surface and an exterior surface thereon wherein said proximal end includes an opening therein that is larger than an opening in said distal end;
   plunger rod assembly including a piston member and an elongate plunger rod, said piston member being slidably disposed in said interior surface of said barrel member to control the flow of fluids through said distal end of said barrel member and said plunger rod having distal and proximal ends and said piston member is operatively connected said plunger rod and said plunger rod extends proximally therefrom beyond said proximal end of said barrel member, said piston member being movable from a first position blocking the flow of fluid through said distal end to a second position allowing the flow of fluid through said distal end;
   barrier means operatively formed distally of said proximal end of said barrier member to prevent the contamination of said interior surface of said barrel member whereby said barrier means is operative when said piston member is in said first position and inoperative when said piston member is in said second position; and
   said barrier means is formed by sealing engagement between a radially inwardly extending lip member on said proximal end of said barrel member and a radially outwardly extending flexible disc member oriented along said plunger rod.

5. The medical device of claim 4 wherein said barrier means is formed by a first member on said plunger rod and a second member on said interior surface of said barrel-member and wherein an enlarged flange on said plunger rod is spaced apart from said first member proximally along said plunger rod whereby said flange contacts said proximal end of said barrel member and said first member contacts said second member when said piston member is adjacent said distal end of said barrel member.

6. The medical device of claim 5 wherein said flange is heat staked to said proximal end of said barrel member to form a tamper-evident indicator therewith.

7. The medical device of claim 4 wherein said barrier means forms a proximal barrier to protect said interior surface of said barrel from contamination and a distal barrier is formed adjacent to said distal end of said barrier to prevent the contamination of a passageway formed in said distal end of said barrel member.

8. The medical device of claim 7 further including a needle sheath operatively mounted on said distal end of said barrel member wherein said distal barrier is formed by operative contact between said needle sheath and said distal end of said barrel member.

9. A medical device comprising:
   an elongate and tubular barrel member having a reduced diameter distal end having a passageway therethrough and an open proximal end, said barrel member including an interior surface and an exterior surface thereon and wherein said opening on said proximal end is larger than said opening in said distal end;
   plunger rod assembly including a piston member and an elongate plunger rod, said piston member being slidably disposed in said interior surface of said barrel member to control the flow of fluids through said passageway at said distal end of said barrel member and said plunger rod having distal and proximal ends and said piston member is operatively connected said plunger rod and said plunger rod extends proximally therefrom beyond said proximal end of said barrel member, said plunger rod assembly being movable from a first position wherein said piston member is blocking the flow of fluids through said passageway at said distal end of said barrel member to a second position wherein said piston member is allowing the flow of fluids through said passageway at said distal end of said barrel member;

proximal barrier means operatively formed generally adjacent said proximal end of said barrel member by a radially outwardly extending flexible disc member on said plunger rod sealingly engages a radially inwardly extending lip member on said interior surface of said barrel member to prevent the contamination of said interior surface of said barrel member whereby said barrier means is operative when said plunger rod assembly is in said first position and inoperative when said plunger rod assembly is in said second position; and distal barrier means formed generally adjacent said distal end of said barrel member by operative contact between said distal end of said barrel member and a needle assembly including an elongate needle sheath and an elongate needle having a needle hub thereon whereby said distal barrier means prevents the contamination of said interior surface of said barrel member distally of said piston member.

10. The medical device of claim 9 wherein said plunger rod includes a reduced diameter area generally adjacent said flexible member on said plunger rod.

11. The medical device of claim 9 wherein said proximal end of said barrel member includes an enlarged finger flange thereon and said plunger rod includes at least one enlarged flange thereon oriented on said plunger rod such that when said piston member is adjacent said distal end of said barrel member, said enlarged flange operatively contacts said finger flange.

* * * * *